United States Patent
Bruder et al.

(10) Patent No.: US 7,505,553 B2
(45) Date of Patent: Mar. 17, 2009

(54) METHOD FOR TAKING COMPUTED TOMOGRAPHY SCANS WITH THE AID OF A CT UNIT, AND A CT UNIT

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 263 days.

(21) Appl. No.: 11/100,445

(22) Filed: Apr. 7, 2005

(65) Prior Publication Data

US 2005/0238136 A1 Oct. 27, 2005

(30) Foreign Application Priority Data

Apr. 8, 2004 (DE) .................. 10 2004 017 540

(51) Int. Cl.
*A61B 6/03* (2006.01)
(52) U.S. Cl. ........................................... 378/11
(58) Field of Classification Search ............... 378/4, 378/11, 12, 15, 16, 901, 113, 137, 14; 382/131
See application file for complete search history.

(56) References Cited

U.S. PATENT DOCUMENTS

| | | | |
|---|---|---|---|
| 5,625,661 A | 4/1997 | Oikawa | |
| 6,256,369 B1 | 7/2001 | Lai | |
| 6,272,199 B1 * | 8/2001 | Sembritzki et al. | 378/14 |
| 6,658,081 B2 | 12/2003 | Bruder et al. | |
| 6,735,273 B2 | 5/2004 | Flohr et al. | |
| 2002/0141628 A1 | 10/2002 | Bruder et al. | |
| 2003/0053597 A1 | 3/2003 | Flohr et al. | |
| 2003/0133533 A1 * | 7/2003 | Bruder et al. | 378/4 |
| 2004/0081279 A1 * | 4/2004 | Brunnett | 378/98.8 |
| 2004/0114707 A1 | 6/2004 | Bruder at al. | |
| 2004/0240719 A1 * | 12/2004 | Gruebnau et al. | 382/131 |
| 2005/0100132 A1 * | 5/2005 | Block et al. | 378/124 |

FOREIGN PATENT DOCUMENTS

DE 198 51 556 A1 5/2000

(Continued)

OTHER PUBLICATIONS

German Office Action (dated Apr. 23, 2007) for counterpart German Patent application No. 10 2004 017 540.3-44.

(Continued)

*Primary Examiner*—Chih-Cheng G Kao
(74) *Attorney, Agent, or Firm*—Harness, Dickey & Pierce, P.L.C.

(57) ABSTRACT

A method is for taking computed tomography scans with the aid of a CT unit and to a CT unit. An X-ray tube is moved in a circle or spiral about a z-axis in combination with a detector situated opposite and an object is scanned. The X-ray tube includes a jumping focus with two or more different jumping focal positions relative to the X-ray tube. Parallel data records are formed from the detector data obtained, and tomograms are reconstructed therefrom. When forming the parallel data records, account is taken of the different position of the respectively current jumping focus in relation to the X-ray tube (=jumping focal position) in the radial direction.

15 Claims, 6 Drawing Sheets

FOREIGN PATENT DOCUMENTS

| | | |
|---|---|---|
| DE | 19953613 A1 * | 5/2001 |
| DE | 29923967 | 6/2001 |
| DE | 299 23 967 U1 | 10/2001 |
| DE | 100 48 775 A1 | 4/2002 |
| DE | 101 26 638 A1 | 9/2002 |
| DE | 101 27 269 A1 | 1/2003 |
| DE | 102 44 181 A1 | 4/2004 |
| DE | 102 45 578 A1 | 8/2004 |
| WO | WO 98/30980 A1 | 7/1998 |

OTHER PUBLICATIONS

Karl Stierstorfer, et al., "Weighted FBP—a simple approximate 3D FBP algorithm for multislice spiral CT with good dose usage for arbitrary pitch," 2004 *Phys. Med. Biol.* 49 pp. 2209-2218, published May 19, 2004.

* cited by examiner

METHOD FOR TAKING COMPUTED TOMOGRAPHY SCANS WITH THE AID OF A CT UNIT, AND A CT UNIT

The present application hereby claims priority under 35 U.S.C. § 119 on German patent application number DE 10 2004 017 540.3 filed Apr. 8, 2004, the entire contents of which is hereby incorporated herein by reference.

FIELD OF THE INVENTION

The invention generally relates to a method for taking computed tomography scans with the aid of a CT unit, and/or to a CT unit. Preferably, an X-ray tube is moved in a circle or spiral about a z-axis in combination with a detector situated opposite, and scans an object, the X-ray tube having a jumping focus with two or more different jumping focal positions relative to the X-ray tube, with parallel data records being formed from the detector data obtained, and with tomograms being reconstructed therefrom.

BACKGROUND OF THE INVENTION

Patent specifications U.S. Pat. No. 5,625,661, U.S. Pat. No. 6,256,369 B1 and the utility model specification DE 299 23 967 U1 from the applicant, the entire contents of which are hereby incorporated herein by reference, disclose computed tomography units that have X-ray tubes with jumping foci.

U.S. Pat. No. 5,625,661 indicates a CT unit in which the focus can jump in the z-direction to a number of different focal positions relative to the X-ray tube so that, in accordance with the variation in the focal position in conjunction with an identical multirow detector situated opposite, a number of beam paths are produced that result in improved scanning of an examination object. The displacement of the focal position of the jumping focus takes place in this case exclusively in the z-direction, the course of the beam remaining unchanged in the radial or azimuthal direction.

Patent specification U.S. Pat. No. 6,256,369 B1 likewise discloses a CT unit with a jumping focus, an X-ray tube also being shown here in FIG. 1, whose jumping focus moves in the xy-plane at a constant distance from the detector, that is to say perpendicular to the system axis. No movement takes place here in the radial direction.

Finally, the utility model specification DE 299 23 967 U1 exhibits different variants of a CT unit with a jumping focus, a displacement in the radial direction also being shown here in addition to the displacements of the focus in the xy plane and in the z-direction.

SUMMARY OF THE INVENTION

Although all the background documents may exhibit the basic possibility of CT designs with a jumping focus, it is not recorded in the prior art how the improved scanning of an examination object is used to actually calculate CT images, nor how the data collection and data conditioning required in this case are to be carried out.

It is therefore an object of an embodiment of the invention to describe a method for taking computed tomography scans with the aid of a CT unit with a jumping focus.

The inventors have found that in forming parallel data records from the detector output data of a detector, in particular a multirow detector, in a CT, whose data have been created with the aid of a jumping focus system, it is particularly important to take account of the fact that different distances from the respective jumping focus to the detector can come about depending on the respective anode geometry and the arrangement thereof, and that these different distances must lead to corresponding computational consequences with reference to the actual ray angle $\theta$ for calculating parallel data records.

The inventors therefore propose, in at least one embodiment, that a method for taking computed tomography scans with the aid of a CT unit, in the case of which an X-ray tube is moved in a circle or spiral about a z-axis in combination with a detector situated opposite, and scans an object, the X-ray tube having a jumping focus with two or more different jumping focal positions relative to the X-ray tube, parallel data records being formed from the detector data obtained, and tomograms being reconstructed therefrom, be improved to the effect that when forming the parallel data records account is taken of the different position of the respectively current jumping focus in relation to the X-ray tube—the jumping focal position—at least in the radial direction. Here, radial direction is understood as the direction of the vector r of a point $P(\alpha, r, z)$ with the cylindrical coordinates $\alpha$, r and z, z corresponding to the system axis, and $\alpha$ representing the angle of rotation of the focus and r the radial distance from the z- or system axis.

In at least one embodiment, when forming the parallel data records, account is also taken of the different position of the respectively current jumping focus in relation to the X-ray tube in the z-direction.

It can be provided in the method according to at least one embodiment of the invention that when compiling the parallel data records, preferably in a first step, an azimuthal rebinning to identical ray angles $\theta$ is carried out separately by jumping focal position and by detector row, the actual radius r, the distance from the detector element considered to the current jumping focal position, of the respective jumping focus featuring in the calculation of the ray angle $\theta$, and data records being interpolated with the aid of an identical $\Delta\theta$ raster. Thus, in accordance with this first step, data records are collected from detector data that all originate from actual or virtual interpolated rays exhibiting a prescribed ray angle $\theta$, and are produced by interpolation if not present. In order to determine the existing ray angle $\theta$ of a ray, account is taken of the small change resulting from the displacement of the focus in relation to the X-ray tube in the radial direction. The formula $\theta=\alpha+\beta$ applies to the ray angle $\theta$, $\alpha$ representing the angle of rotation of the focus, and $\beta$ the fan angle.

However, in the case of this collection of the data records, there is no mixing of data from different readings having different jumping focal positions. Thus, in the case of N jumping focal positions—which naturally migrate in space as the X-ray tube rotates about the examination object—N data records are also produced. Thus, separate data collection and data conditioning are carried out in principle for each of the N jumping focal positions.

If a number of readings of different jumping focal positions have been recorded for an identical z position, it is also possible according to an embodiment of the invention, preferably in a second step, for data records with an identical z-coordinate and an identical ray angle $\theta$ to be interleaved from the focal positions and to be assembled and/or interpolated to form new data records with a closer equidistant $\Delta\theta$ raster.

Furthermore, it can be provided in the method according to an embodiment of the invention that preferably in a third step of the method, a radial rebinning to an identical and equidistant $\Delta p$ raster with $p=R\cdot\sin\beta$ (r=distance from the z axis, $\beta$=fan angle) is carried out with the aid of the data records of all the jumping focal positions. For this purpose, the existing data records, which are certainly sorted in terms of their spatial alignment but do not exhibit a common raster in the p-direction, are sorted in accordance with a prescribed raster, and if there are no rays present at the desired raster points they are produced by interpolating neighboring data.

Finally, the inventors propose that in one embodiment, preferably in a fourth step, data records with a different jumping focal position in the z-direction and with an identical ray angle θ are interleaved and are interpolated to form a data record with a smaller equidistant Δz raster. Thus, if an X-ray source with different jumping focal positions in the z-direction is used, the additionally obtained oversampling in this direction can be used in order to achieve a further improvement in scanning by producing an additional interleaving of the data records and thus a smaller scanning raster.

Subsequently, the data records thus formed can, after they have been conditioned, be fed for the purpose of calculating the tomograms to a reconstruction method known per se, for example an AMPR (AMPR=Adaptive Multiple Plane Reconstruction) or SMPR (SMPR=Segmented Multiple Plane Reconstruction) method. Such methods of calculation are generally known and reference may be made, for example, to the German patent applications with the file references DE 101 27 269.3 and DE 101 06 398.9, as well as to the international patent application WO 98/30980, the entire contents of each of which are hereby incorporated herein by reference.

In accordance with a particular variant of the method, the "third step" of the method, specifically rebinning to a common Δp raster can be omitted in the initial data conditioning, and this can be taken into account only on reaching the reconstruction method. According to an embodiment of the invention, it is then possible to carry out equidistant rastering, for example in a two-dimensional interpolation method in the z- and p-directions.

Alternatively, the "third step" can also be modified such that the radial rebinning is not performed to a common Δp raster, but is performed to a separate raster for each of the various jumping focal positions in the z-direction. It is possible thereby, if appropriate, to reduce the outlay on interpolation in this step, although in this case the different rastering has to be taken into account in the following reconstruction. This can be done, for example, by two-dimensional interpolation during the reconstruction in the z- and p-directions.

It has proved to be advantageous, furthermore, when for scanning purposes use is made of a jumping focus with at least 2 jumping focal positions in the azimuthal direction, and at least 2 jumping focal positions in the z-direction, it being particularly advantageous when use is made of a jumping focus each of whose individual jumping focal positions has different azimuthal coordinates and z-coordinates. A particularly high level of oversampling can be achieved thereby, in which case redundant measurements can largely be avoided by way of congruent ray paths that supply no additional information.

Thus, overall, the above-described method employs the improved oversampling by the use of jumping foci for the CT scanning of an object with the aid of a multirow detector, doing so even for the conditioning of the image data, an improved resolution and the reduction of artifacts such as windmill structures in the CT image, for example, being achieved.

In accordance with an idea of an embodiment of the invention, the inventors also further propose a computed tomography unit comprising an X-ray tube that is moved in a circle or spiral about a z-axis in combination with a multirow detector situated opposite, and scans an object, the X-ray tube having a jumping focus with two or more different jumping focal positions relative to the X-ray tube, and means for reconstructing tomograms from detector data obtained, with prior formation of parallel data records. It further may include means that can execute the method according to the invention during operation.

BRIEF DESCRIPTION OF THE DRAWINGS

The invention is explained in more detail below with the aid of the figures and using the example embodiments, and it may be pointed out here that only those elements essential for directly understanding the invention are shown. The following reference symbols are used in this case: a: jumping focal position in z-direction, b: jumping focal position in z-direction, B: examination object; D: detector; F: focus; $F_1$ to $F_6$: focal positions; p: distance of the ray from the z-axis; Q: surface perpendicular to central ray; r: radius/distance of the focus from the z-axis; S: X-ray; $S_z$: central ray; t: time progression; z: system axis: α: angle of rotation; β: fan angle; φ: angle of inclination of the ray to the z-axis; θ: ray angle.

In detail, in the drawings.

DETAILED DESCRIPTION OF THE EXAMPLE EMBODIMENTS

Figure 1:
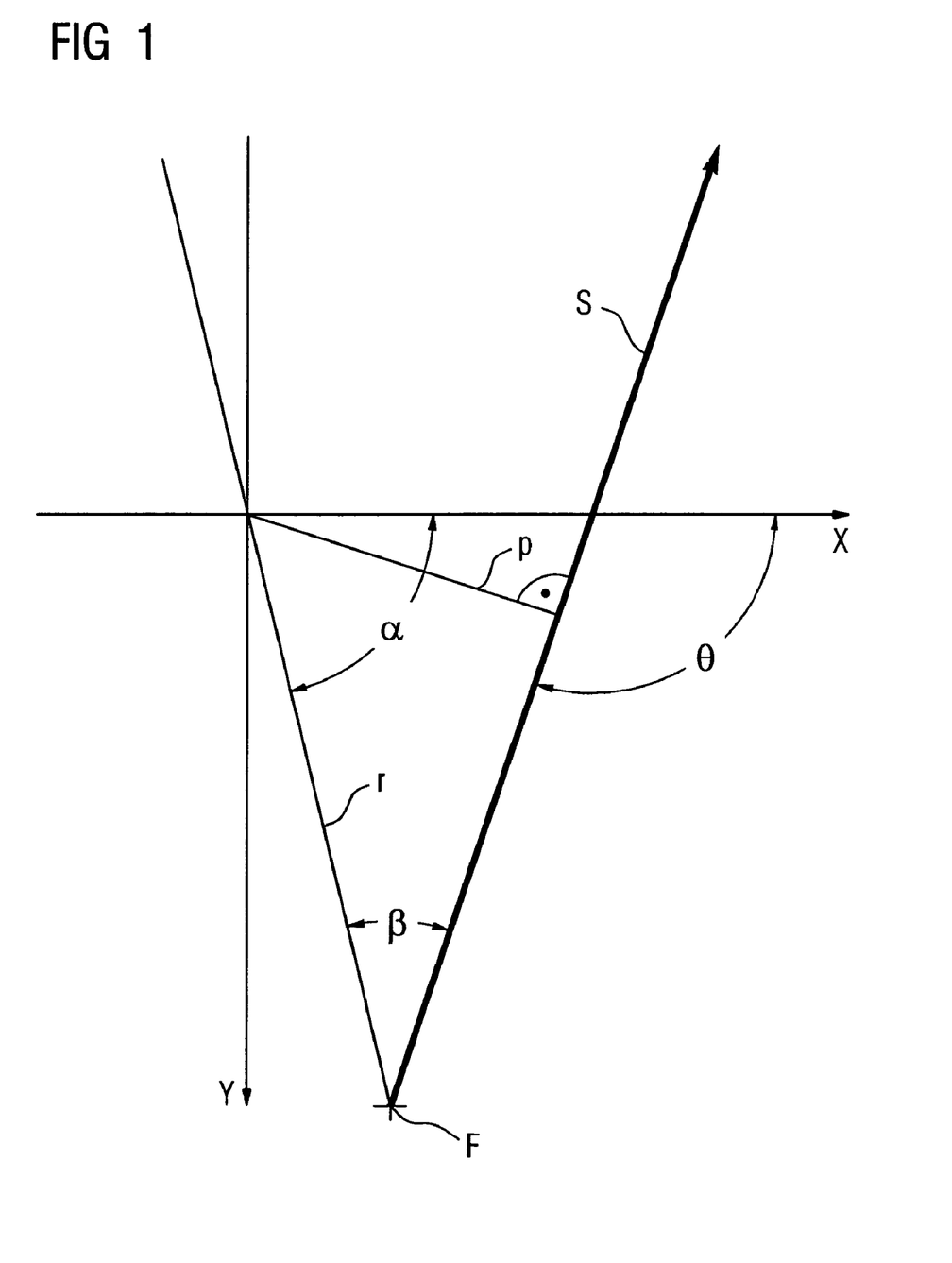
FIG. 1 shows an illustration of the geometry used.

FIG. 1 shows the geometry used in this application. An x/y coordinate system is illustrated whose z-axis, which is perpendicular to the x/y plane and also represents the system axis of the CT, projects from the paper at the origin. The position of the focus F is defined by the radius r from the z-axis and the angle of rotation α about the z-axis. The position of the X-ray S is determined in the surface by the fan angle β and the distance p from the origin. The fan angle β between the x-axis and the X-ray S is determined in each case by the position of the focus F and the detector element respectively under consideration. In addition, the angle of inclination φ of the X-ray S about the x-axis results from the position of the respectively considered detector row and the z-position of the focus.

Figure 2:
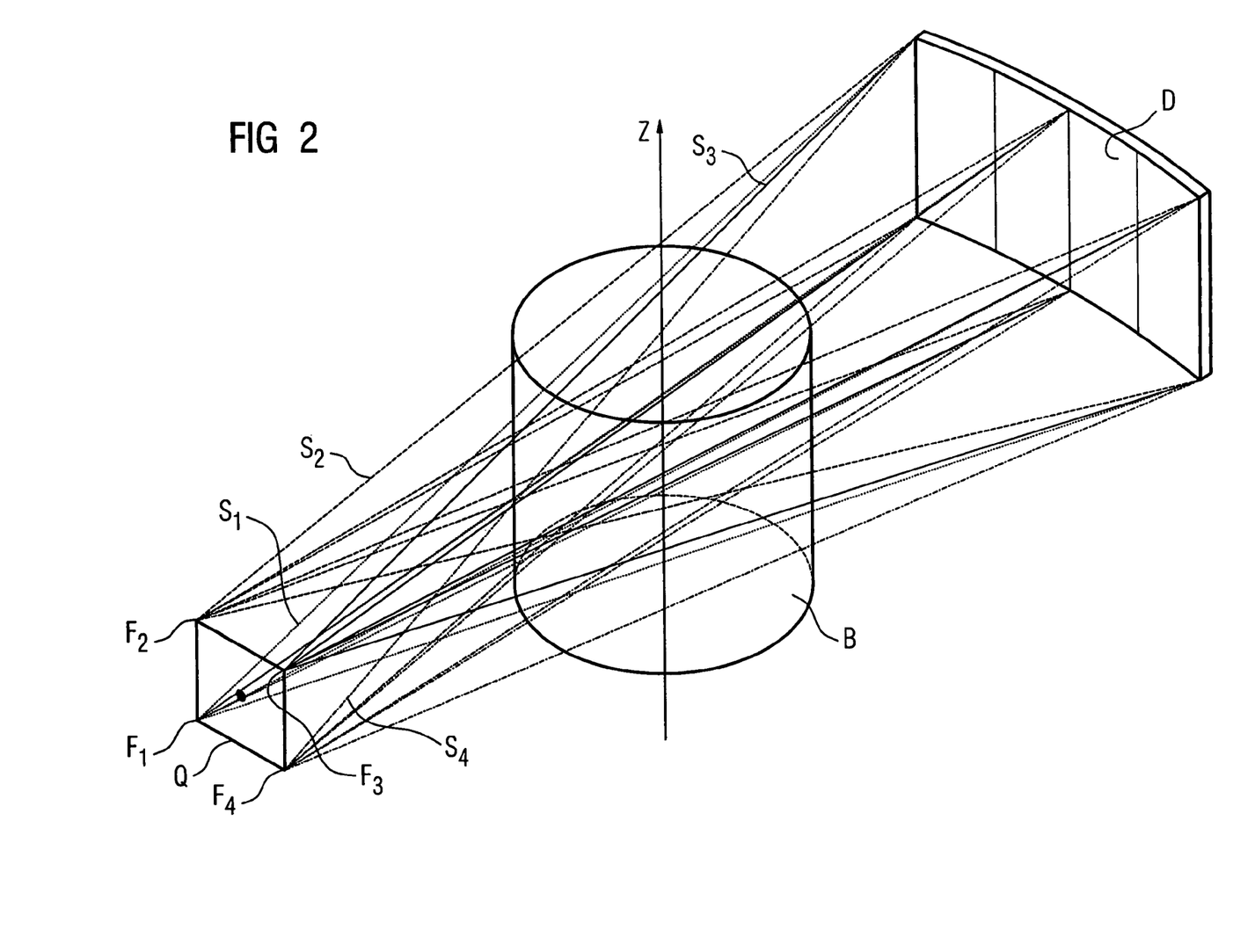
FIG. 2 shows an illustration of four ray fans formed by a jumping focus with four different focal positions.

FIG. 2 shows in accordance with the inventive method a schematic of an exemplary jumping focus with four different focal positions $F_1$ to $F_4$, each of which emits X-rays onto a detector situated opposite, and which penetrate an examination object B. For the purpose of adequate clarity, only six marginal rays S are illustrated between the individual focal positions $F_1$ to $F_4$ and the detector D. According to an embodiment of the invention, in the previously described method the change in the radial distance of the individual focal positions from the z-axis in the respective jumping focal positions $F_1$ to $F_4$ is taken into account in the calculation when forming parallel data records from the collected ray data.

Thus, by contrast with the systems/methods in which the jumping focal positions are regarded by way of simplification only as variable or offset in the z-direction, something which leads to marked losses of definition and artifacts outside the center of rotation, account may now be taken of the radial displacement of the focus to the extent that the actual location of the focus and the actual fan angle β calculated therefrom feature in the conversion of the data to parallel data. The loss of definition and artifacts that otherwise occur are thereby avoided.

The aim in the following FIGS. 3 to 18 is illustrate different jumping focal positions that can be used with the method according to at least one embodiment of the invention.

Figure 3:
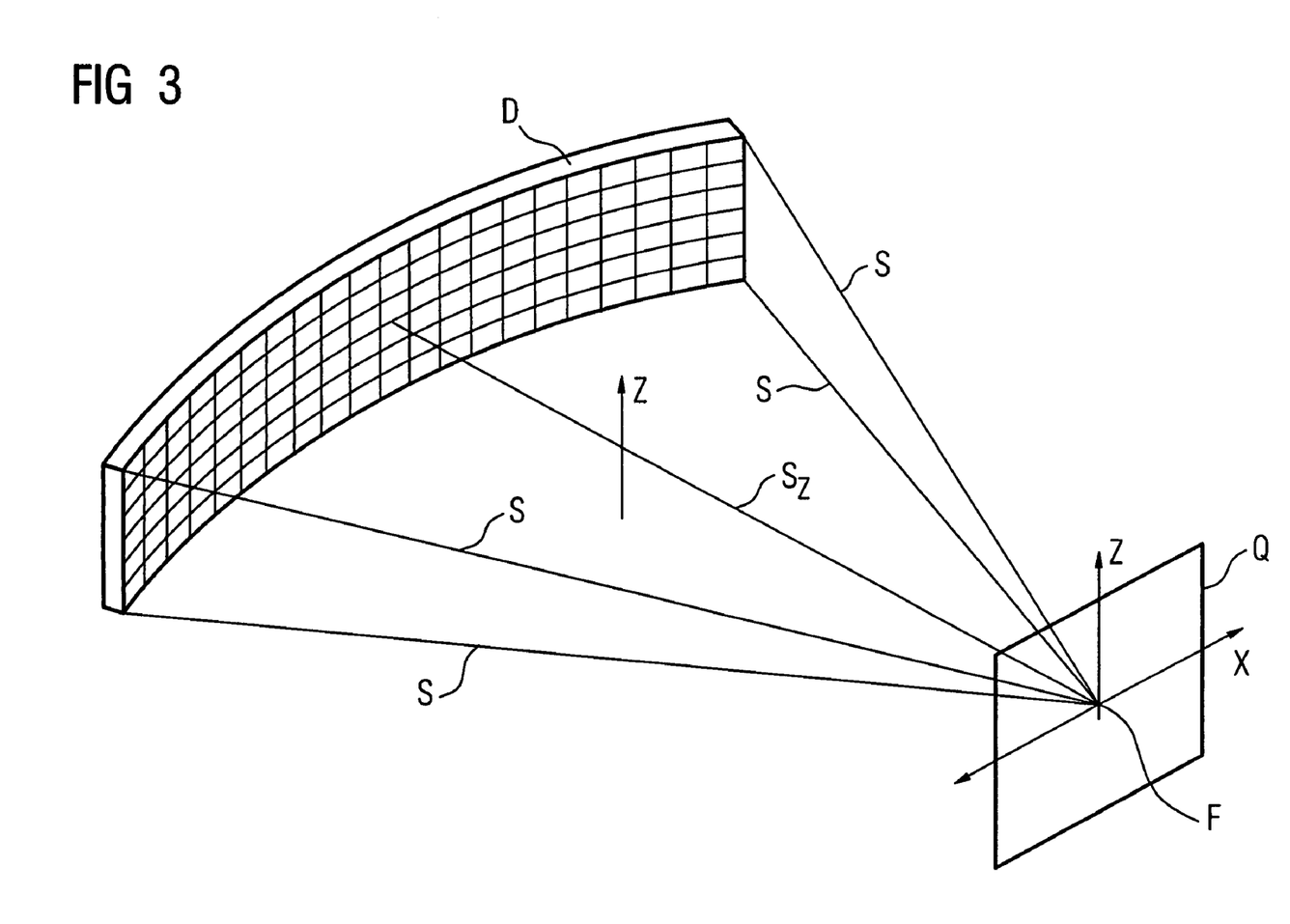
FIG. 3: shows an illustration relating to the orientation of the jumping focal positions of FIGS. 4 to 19.
Figures 4, 8:
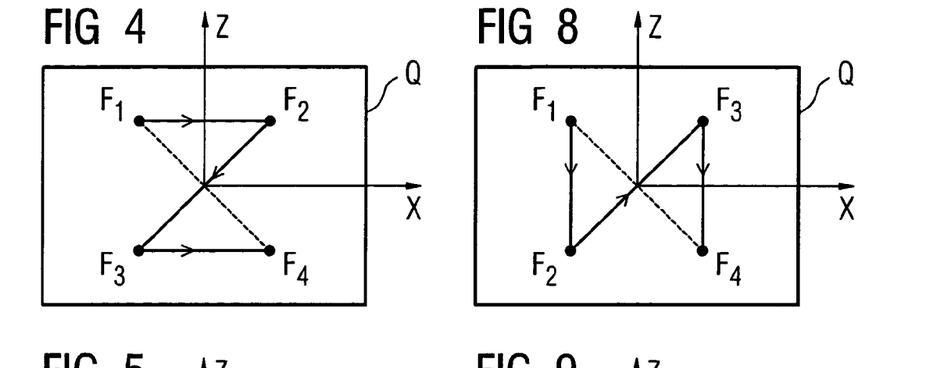
FIG. 4 to FIG. 19: show variants of different jumping focal positions.
Figures 5, 9:
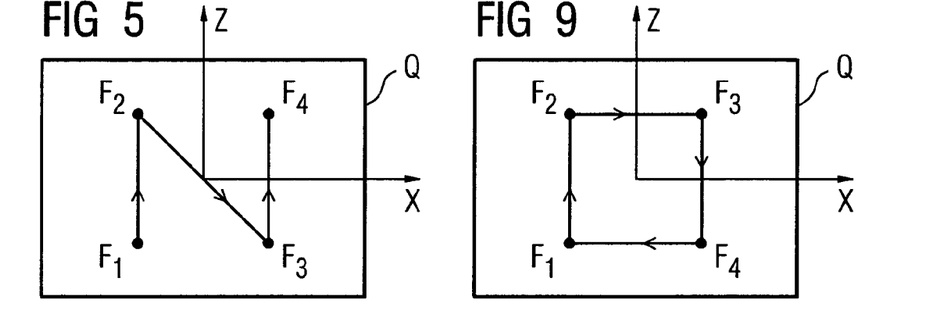
Figures 6, 10:
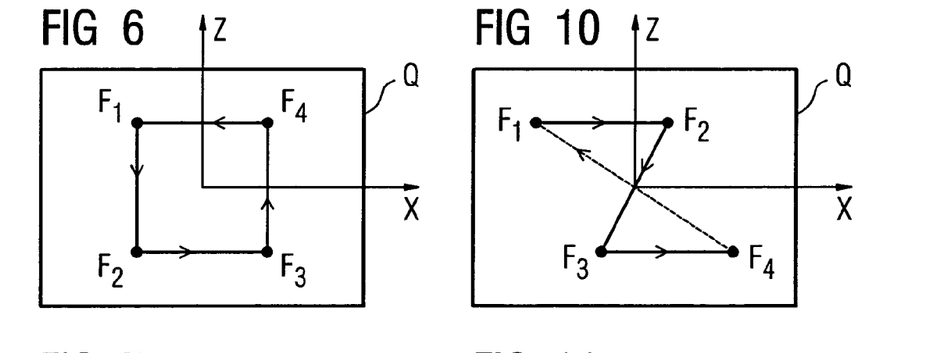
Figures 7, 11:
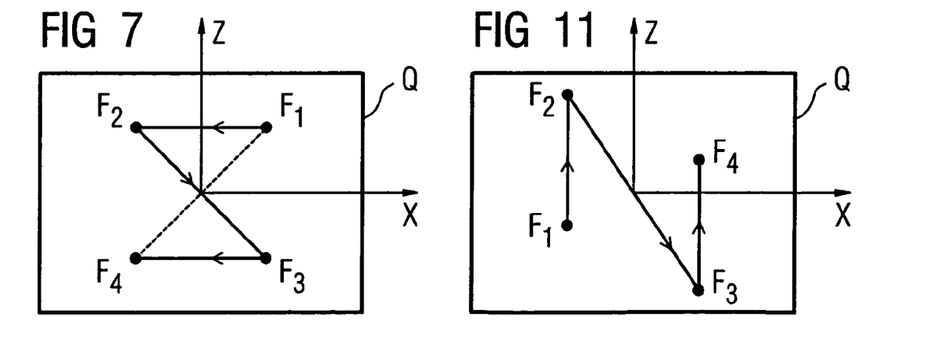
Figure 12:
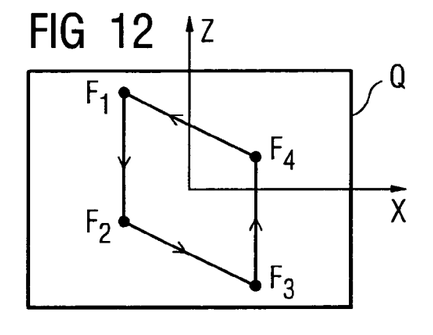
Figure 13:
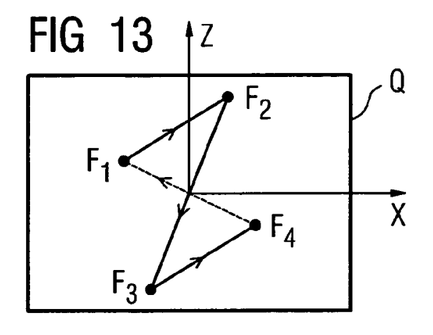
Figure 14:
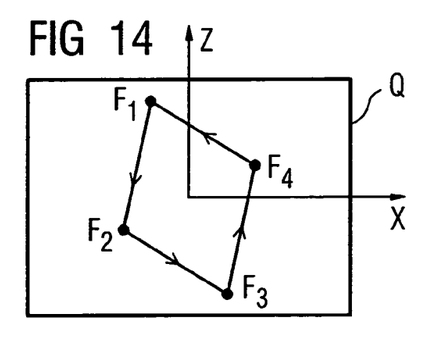

For the variants of jumping focal positions illustrated below, FIG. 3 shows by way of orientation a detector D on which the marginal rays S emanating from a single central focus F impinge, and a centrally situated central ray $S_z$ that is perpendicular to the system axis z, and a surface Q passing through the focus F and which is defined by an x-axis and a z-axis. Illustrated by way of example in FIGS. 4 to 14 in relation to this surface Q are variants of jumping focal positions $F_1$ to $F_6$, FIGS. 4 to 9 showing four jumping focal positions $F_1$ to $F_4$ that correspond to the corner points of a rectangle, and the sequence of activation of the respective jumping focal position being illustrated by the connecting arrows between the jumping focal positions.

FIGS. 10 to 14 likewise show the positions of a jumping focus with four jumping focal positions $F_1$ to $F_4$, whose positions correspond in each case to the corner points of a rhombus. Here, as well, the sequence of the jumping of the individual positions is illustrated by arrows.

Figure 15:
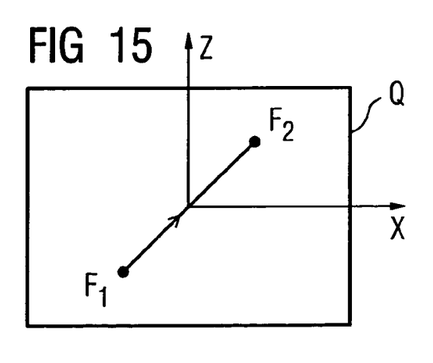
Figure 16:
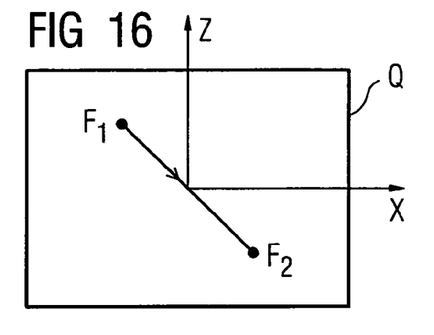

FIGS. 15 and 16 show a possibility of variation in which two jumping focal positions $F_1$ and $F_2$ can jump out of the zx-plane, the illustrated number of the jumping focal positions being intended as only exemplary, and it likewise being possible to make use of further jumping focal positions in space.

Figure 17:
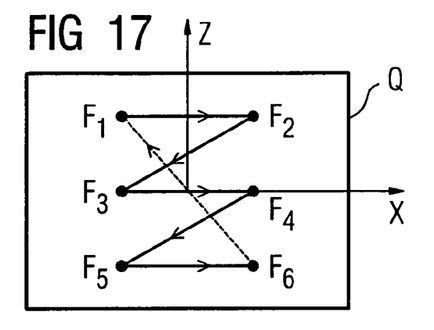
Figure 18:
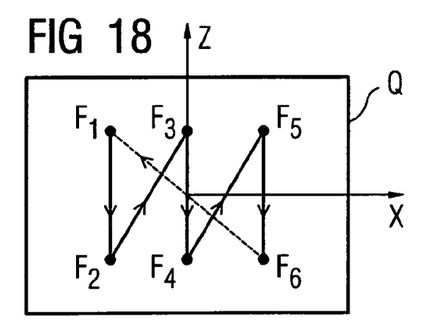

FIGS. 17 and 18 also illustrate by way of example a variant of a jumping focus with six focal positions $F_1$ to $F_6$, these illustrations that are shown showing only some of the possible variations. It is essential in the case of the method according to an embodiment of the invention that the different positions of the jumping focus result in each case in different distance vectors of the jumping focal position, and that these vectors result from the calculation of the ray path and the ray orientation, in particular the fan angle β, resulting therefrom.

It is to be pointed out that the positions shown for the jumping focus can be arranged arbitrarily, and are not restricted to the examples shown, since in accordance with the invention the respective actual position of the foci features in the calculation.

Figure 19:
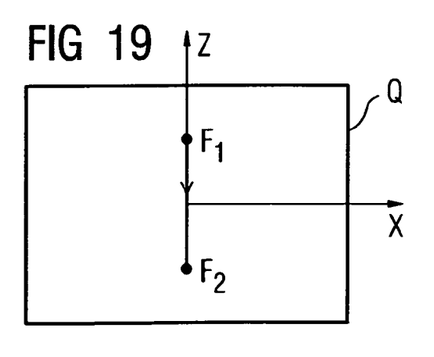
Figure 20:
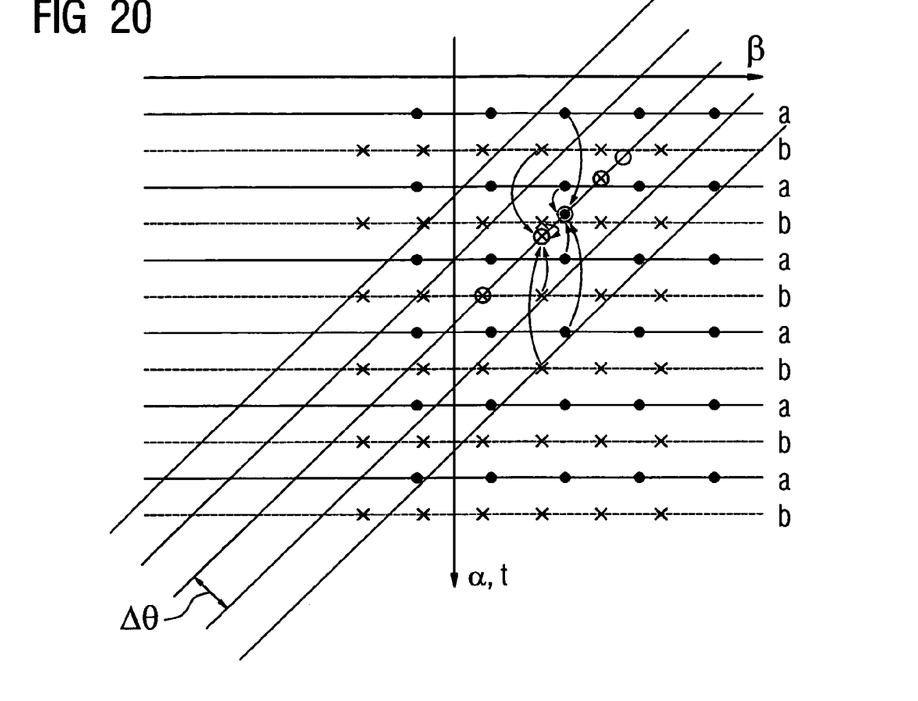
FIG. 20: shows a schematic of the rebinning to a constant Δθ raster.
Figure 21:
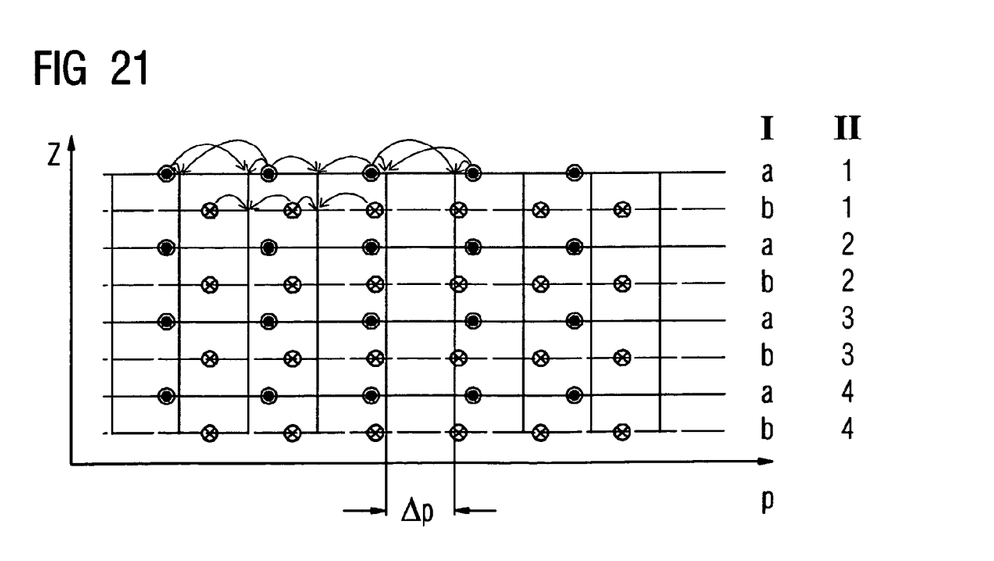
FIG. 21 shows a schematic of the rebinning to a constant Δp raster.

FIG. 19 shows a further variant of the spatial arrangement of two jumping focal positions $F_1$ to $F_2$ along the z-axis, as a foundation for the interpolations shown in FIGS. 20 and 21. However, it is to be pointed out that the invention is not restricted to this spatial arrangement of the jumping focal positions.

FIG. 20 shows the inventive influence of taking account of the altered radial position of the jumping focus for forming the parallel data records. A rectangular coordinate system is shown in which the fan angle β is plotted on the abscissa, and the ordinate corresponds to the angle of rotation α of the focus, to be exact to the angle of rotation of the jumping focus considered, the starting angle from which the angle of rotation is counted being identical for all jumping focal positions. By contrast with earlier considerations of individual foci, the angle of rotation can here no longer be assigned uniquely to the time profile t, since at the identical instant t different jumping foci have different angles of rotation α.

The horizontal continuous lines show the measuring points of an arbitrarily extracted single detector row, the individual points constituting measuring points corresponding to the detector elements and all the measuring points • on the continuous lines corresponding to a first jumping focal position a. Likewise illustrated, on the dashed lines, are the measuring points x of the same detector row, although on the one hand temporally shifted, and on the other hand slightly compressed toward the α-axis because of the different jumping focal position b that produces these measuring points. This slight compression or else shifting of the measuring points x between the two jumping focal positions shows the variation in the ray fan owing to the altered focal position in the radial direction.

The continuous lines arranged at an angle of approximately 45° correspond to the positions of rays with an identical θ=α+β.

According to an embodiment of the invention, there now takes place a rebinning, that is to say an interpolation of the measured values of identical jumping focal positions a and b, respectively, on the line with constant θ, a distinction continuing to remain between the data of the individual foci by ringing these new data with an additional circle in accordance with their original symbol. Thus, for a better overview the interpolation results of this method step are indicated by two representative points ⊙ and ⊗, an interpolation value ⊙ and ⊗ actually resulting during the calculation in each case for each crossing point of the oblique lines with the imaginary perpendicular at the points • and x. The arrows drawn in are intended to indicate an exemplary interpolation by four neighboring measuring points of identical jumping focal position.

It follows that the rebinning illustrated here corresponds to a measuring situation having a jumping focus with two different jumping focal positions in accordance with FIG. 19, which are offset in the z-direction. However, it is also possible in the same way to proceed with measurements with a jumping focus having 2×2 jumping focal positions, such as are described, for example, in one of FIGS. 1 to 14, although interleaving in the β-direction must firstly take place. It is also to be remarked here that other interpolation methods are likewise possible and so, for example, a 2d interpolation over neighboring measuring points from an identical focal position can be carried out.

After this rebinning as carried out above, data records are present that have a constant Δθ raster, the latter being represented by the obliquely running lines with the spacing Δθ.

This data record is now plotted in FIG. 21 in a coordinate system where the abscissa corresponds to the p-coordinate, and the ordinate corresponds to the system axis or z-axis, with measured values of different jumping focal positions also continuing to differ in terms of data record.

The measuring points or, more accurately, interpolation results from the method in accordance with FIG. 20, that are illustrated with a central point and circle, correspond to a first focal position a, while the crosses with a circle are assigned to a further focal position b. Identical point illustrations were in each case recorded here for identical jumping focal positions. Illustrated on the right next to the plotting of the measuring points are two columns I and II, the respective jumping focal positions being entered in column I, while the assignment to the corresponding detector row is entered in column II.

According to an embodiment of the invention, these interpolation data are now interpolated once again onto a prescribed Δp raster such that parallel rays with a uniform Δp raster are present in the final analysis, and these can be used for the further reconstruction for CT scans. FIG. 21 illustrates the Δp raster by the equidistant perpendicular lines, and the crossing points thereof by the horizontal lines, which respectively correspond to a detector row.

It remains to be pointed out in addition that the interpolations can be undertaken in many different ways. An interpolation over neighboring points of an identical row or column is indicated in FIGS. 20 and 21 by the arrows drawn in, but it is also possible to use all the points in a specific circumcircle, or only two immediately adjacent neighboring points for the interpolation. What is finally obtained is an equidistant raster of interpolation points that corresponds to the crossing points in FIG. 21. This raster can then be used to carry out the reconstruction in a known way, the actual spatial offset of the jumping focal positions, and their geometrical effect now being taken into account in the calculation.

Overall, therefore, an embodiment of the invention proposes a method for conditioning CT data that are determined by jumping focus X-ray tubes, which leads to a substantial improvement in image quality on the basis of taking account of the change in the different relative position of the current jumping focus in the radial direction, and on the basis of the accurate calculation, associated therewith, of the radial angle $\beta$ and the ray positions.

It is self-evident that the abovementioned features of the invention can be used not only in the combination respectively specified, but also in other combinations or alone, without departing from the scope of the invention. It is self-evident, furthermore, that a CT unit within the meaning of the invention is to be understood not only as the classic X-ray computed tomography unit with a closed gantry, but also as so called C-arc units.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

LIST OF REFERENCE SYMBOLS a Jumping focal position in z-direction
b Jumping focal position in z-direction
B Examination object
D Detector
F Focus
$F_1$ to $F_6$ Focal positions
p Distance of the ray from the z-axis
Q Surface
r Radius/distance of the focus
S X-ray
$S_z$ Central ray
t Time progression
z System axis
$\alpha$ Angle of rotation
$\beta$ Fan angle
$\phi$ Angle of inclination
$\theta$ Ray angle Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for taking computed tomography scans with the aid of a CT unit including an X-ray tube movable in at least one of a circle and spiral about a z-axis in combination with a detector situated opposite the X-ray tube, the X-ray tube including a jumping focus with at least two different jumping focal positions relative to the X-ray tube, the method comprising:

forming parallel data records from detector data obtained from scanning an object with the X-ray tube, such that the different positions of a respectively current jumping focus in relation to the X-ray tube in a radial direction are taken into account when forming the parallel data records; and reconstructing tomograms from the parallel data records; wherein when compiling the parallel data records, an azimuthal parallel rebinning to identical ray angles $\theta$ is carried out separately by jumping focal position and by detector row, the actual radius of the respective jumping focus featured in the calculation of the ray angle $\theta$, and data records being interpolated with the aid of an identical $\Delta\theta$ raster.

2. The method as claimed in claim 1, wherein, when forming the parallel data records, account is taken of the different position of the respectively current jumping focus in relation to the X-ray tube in the z-direction.

3. The method as claimed in claim 2, wherein data records with an identical z-coordinate and an identical ray angle $\theta$ are interleaved from the focal positions and are assembled and/or interpolated to form new data records with a closer equidistant $\Delta\theta$ raster.

4. The method as claimed in claim 1, wherein data records with an identical z-coordinate and an identical ray angle $\theta$ are interleaved from the focal positions and are assembled and/or interpolated to form new data records with a closer equidistant $\Delta\theta$ raster.

5. The method as claimed in claim 4, wherein a radial rebinning to an identical and equidistant $\Delta p$ raster with $p=R \cdot \sin\beta$ is carried out with the aid of the data records of all the jumping focal positions, and wherein R is a distance from the z axis and $\beta$ is a fan angle.

6. The method as claimed in claim 5, wherein a jumping focus with at least 2 jumping focal positions in an azimuthal direction and at least 2 jumping focal positions in the z-direction is used for taking the computed tomography scans.

7. The method as claimed in claim 6, wherein each individual jumping focal position of the jumping focus has different azimuthal coordinates and z-coordinates.

8. A computer-readable medium including a computer program that, when executed on a computer, causes the computer to carry out the method as claimed in claim 1.

9. A method for taking computed tomography scans with the aid of a CT unit including an X-ray tube movable in at least one of a circle and spiral about a z-axis in combination with a detector situated opposite the X-ray tube, the X-ray tube including a jumping focus with at least two different jumping focal positions relative to the X-ray tube, the method comprising:

forming parallel data records from detector data obtained from scanning an object with the X-ray tube, such that the different positions of a respectively current jumping focus in relation to the X-ray tube in a radial direction are taken into account when forming the parallel data records; and reconstructing tomograms from the parallel data records; wherein data records with an identical z-coordinate and an identical ray angle θ are interleaved from the focal positions and are assembled and/or interpolated to form new data records with a smaller equidistant Δθ raster.

10. A computer-readable medium including a computer program that, when executed on a computer, causes the computer to carry out the method as claimed in claim 9.

11. A method for taking computed tomography scans with the aid of a CT unit including an X-ray tube movable in at least one of a circle and spiral about a z-axis in combination with a detector situated opposite the X-ray tube, the X-ray tube including a jumping focus with at least two different jumping focal positions relative to the X-ray tube, the method comprising:

forming parallel data records from detector data obtained from scanning an object with the X-ray tube, such that the different positions of a respectively current jumping focus in relation to the X-ray tube in a radial direction are taken into account when forming the parallel data records; and reconstructing tomograms from the parallel data records; wherein a radial rebinning to an identical and equidistant Δp raster with p=R·sinβ is carried out with the aid of the data records of all the jumping focal positions, and wherein R is a distance from the z axis and β is a fan angle.

12. A computer-readable medium including a computer program that, when executed on a computer, causes the computer to carry out the method as claimed in claim 11.

13. A method for taking computed tomography scans with the aid of a CT unit including an X-ray tube movable in at least one of a circle and spiral about a z-axis in combination with a detector situated opposite the X-ray tube, the X-ray tube including a jumping focus with at least two different jumping focal positions relative to the X-ray tube, the method comprising:

forming parallel data records from detector data obtained from scanning an object with the X-ray tube, such that the different positions of a respectively current jumping focus in relation to the X-ray tube in a radial direction are taken into account when forming the parallel data records; and reconstructing tomograms from the parallel data records; wherein data records with a different jumping focal position in the z-direction and with an identical ray angle θ are interleaved and are interpolated to form a data record with a smaller equidistant Δz raster.

14. A computer-readable medium including a computer program that, when executed on a computer, causes the computer to carry out the method as claimed in claim 13.

15. A computed tomography unit comprising:

an X-ray tube, movable in at least one of a circle and spiral about a z-axis in combination with a multirow detector situated opposite thereof, and adapted to scan an object, the X-ray tube having a jumping focus with at least two different jumping focal positions relative to the X-ray tube; and means for reconstructing tomograms from parallel data records formed from detector data obtained from scanning the object with the X-ray tube, wherein the different positions of a respectively current jumping focus in relation to the X-ray tube in a radial direction are taken into account when forming the parallel data records; wherein when compiling the parallel data records, the computer tomography unit carries out an azimuthal parallel rebinning to identical ray angles θ separately by jumping focal position and by detector row, the actual radius of the respective jumping focus featured in the calculation of the ray angle θ, the data records being interpolated with the aid of an identical Δθ raster.

* * * * *